United States Patent
Kurash et al.

(10) Patent No.: US 9,766,236 B2
(45) Date of Patent: Sep. 19, 2017

(54) TASTE RECEPTOR INTERNALIZATION ASSAY

(71) Applicant: PepsiCo, Inc., Purchase, NY (US)

(72) Inventors: Yuliya Kurash, Purchase, NY (US); Stephen Gravina, Purchase, NY (US)

(73) Assignee: PEPSICO, INC., Purchase, NY (US)

(*) Notice: Subject to any disclaimer, the term of this patent is extended or adjusted under 35 U.S.C. 154(b) by 0 days.

(21) Appl. No.: 14/890,054

(22) PCT Filed: May 9, 2014

(86) PCT No.: PCT/US2014/037507
§ 371 (c)(1),
(2) Date: Nov. 9, 2015

(87) PCT Pub. No.: WO2014/183041
PCT Pub. Date: Nov. 13, 2014

(65) Prior Publication Data
US 2016/0084834 A1    Mar. 24, 2016

Related U.S. Application Data

(60) Provisional application No. 61/821,978, filed on May 10, 2013.

(51) Int. Cl.
*G01N 33/566* (2006.01)
*C07K 14/705* (2006.01)

(52) U.S. Cl.
CPC .......... *G01N 33/566* (2013.01); *C07K 14/705* (2013.01); *G01N 2500/10* (2013.01)

(58) Field of Classification Search
None
See application file for complete search history.

(56) References Cited

U.S. PATENT DOCUMENTS

| | | |
|---|---|---|
| 6,759,206 B1 | 7/2004 | Rubin et al. |
| 7,022,488 B2 | 4/2006 | Servant et al. |
| 7,297,772 B2 | 11/2007 | Zoller et al. |
| 7,402,400 B2 | 7/2008 | Zuker et al. |
| 7,763,431 B1 | 7/2010 | Zoller et al. |
| 7,799,538 B2 | 9/2010 | Lienhard et al. |
| 7,919,236 B2 | 4/2011 | Slack et al. |
| 8,338,115 B2 | 12/2012 | Adler et al. |
| 2002/0160424 A1 | 10/2002 | Adler et al. |
| 2005/0106571 A1 | 5/2005 | Erlenbach et al. |
| 2005/0244810 A1 | 11/2005 | Egan et al. |
| 2008/0039534 A1 | 2/2008 | Radhakrishna et al. |
| 2008/0248996 A1 | 10/2008 | Zoller et al. |
| 2009/0075927 A1 | 3/2009 | Liao et al. |
| 2009/0117563 A1 | 5/2009 | Moyer et al. |
| 2009/0317858 A1 | 12/2009 | Hanson |
| 2012/0237953 A1 | 9/2012 | Brune et al. |
| 2016/0091488 A1 | 3/2016 | Kurash et al. |

FOREIGN PATENT DOCUMENTS

| | | |
|---|---|---|
| RU | 2010110557 A | 9/2011 |
| WO | WO-0003246 A2 | 1/2000 |
| WO | WO-2004055048 A2 | 7/2004 |
| WO | WO-2006040337 A1 | 4/2006 |
| WO | WO-2007047988 A2 | 4/2007 |
| WO | WO-2007121604 A2 | 11/2007 |
| WO | WO-2007147275 A1 | 12/2007 |
| WO | WO-2008014401 A2 | 1/2008 |
| WO | WO-2009025793 A2 | 2/2009 |
| WO | WO-2010088633 A2 | 8/2010 |
| WO | WO-2011067202 A1 | 6/2011 |
| WO | WO 2012/102900 | 8/2012 |

OTHER PUBLICATIONS

Naik et al., Internalization and recycling of the C5a anaphylatoxin receptor: evidence that the agonist-mediated internalization is modulated by phosphorylation of the C-terminal domain, 1997, Journal of Cell Science 110:2381-2390.*

Lee et al., Tip60 and HDAC7 Interact with the Endothelin Receptor A and May Be Involved in Downstream Signaling*, May 18, 2001, The Journal of Biological Chemistry 276(20):16597-16600.*

Adler, E., et al., "A Novel Family of Mammalian Taste Receptors," *Cell* 100(6)693-702, Cell Press, United States (2000).

International Preliminary Report on Patentability for International Application No. PCT/US2014/037507, The International Bureau of WIPO, Switzerland, issued on Nov. 10, 2015, 6 pages.

International Search Report and Written Opinion for International Application No. PCT/US2014/037507, International Searching Authority, United States, mailed on Oct. 14, 2014, 8 pages.

Zhao, G.Q., et al., "The Receptors for Mammalian Sweet and Umami Taste," *Cell* 115(3)255-266, Cell Press, United States (2003).

Extended European Search Report for EP Application No. 14794217.1, European Patent Office, Munich, Germany, mailed on Nov. 3, 2016, 7 pages.

GenBank, "Taste Receptor Type 1 member 2 Precursor [*Homo sapiens*]," Accession No. NP_689418.2, accessed at http:/www.ncbi.nlm.nih.gov/protein/112789566/, accessed on Jun. 30, 2016, 4 pages.

GenBank, "Taste Receptor type 1 Member 3 Precursor [*Homo sapiens*]," Accession No. NP_689414.1, accessed at http://www.ncbi.nlm.nib.gov/protein/NP_689414.1, accessed on Jun. 30, 2016, 4 pages.

Gershan, J., et al., "Transgene expression in nucleofected cancer cell lines is enhanced by cell division," *Cancer Research* 65(9 Supplement):Abstract 6059, American Association for Cancer Research, United States (2005).

Haasen, D., et al., "G protein-coupled receptor internalization assays in the high-content screening format," *Methods in Enzymology* 414:121-139, Elsevier Inc., United States (2006).

(Continued)

*Primary Examiner* — John Ulm
(74) *Attorney, Agent, or Firm* — Sterne, Kessler, Goldstein & Fox P.L.L.C.

(57) ABSTRACT

This disclosure provides a taste receptor internalization assay useful for identifying taste modulators.

8 Claims, 6 Drawing Sheets

(56) References Cited

OTHER PUBLICATIONS

International Preliminary Report on Patentability for International Application No. PCT/US2014/037511, The International Bureau of WIPO, Switzerland, mailed on Nov. 10, 2015, 7 pages.

International Search Report and Written Opinion for International Application No. PCT/US2014/037511, International Searching Authority, United states, mailed on Oct. 17, 2014, 10 pages.

Jang, H.J., et al., "Gut-expressed Gustducin and Taste Receptors Regulate Secretion of Glucagon-like Peptide-1," *Proceedings of the National Academy of Sciences U.S.A* 104(38):15069-15074, National Academy of Sciences, United States (2007).

Martin, C., et al., "Lipid-mediated release of GLP-1 by mouse taste buds from circumvallate papillae: putative involvement of GPR120 and impact on taste sensitivity," *Journal of Lipid Research* 53(11):2256-2265, American Society for Biochemistry and Molecular Biology, Inc., United States (2012).

Niforou, K.N., et al., "The proteome profile of the human osteosarcoma U2OS cell line," *Cancer Genomics & Proteomics* 5(1):63-78, International Institute of Anticancer Research, Greece (2008).

Ozeck, M., et al., "Receptors for bitter, sweet and umami taste couple to inhibitory G protein signaling pathways," *European Journal of Pharmacology* 489(3):139-149, Elsevier B.V., Netherlands (2004).

Partial Supplementary European Search Report for EP Application No. 14794836.8, European Patent Office, Munich, Germany, mailed on Nov. 7, 2016, 8 pages.

Van Lith, L.H.C., et al., "C5a-stimulated recruitment of β-arrestin2 to the nonsignaling 7- transmembrane decoy receptor C5L2," *Journal of Biomolecular Screening* 14(9):1067-1075, Society for Biomolecular Sciences, United States (2009).

Watts, A.O., et al., "β-Arrestin recruitment and G protein signaling by the atypical human chemokine decoy receptor CCX-CKR," *The Journal of Biological Chemistry* 288(10):7169-7181, American Society for Biochemistry and Molecular Biology, Inc., United States (2013).

Ueda, T., et al., "Functional Interaction between T2R Taste Receptors and G-Protein α Subunits Expressed in Taste Receptor Cells," *The Journal of Neuroscience* 23(19):7376-7380, Society for Neuroscience, United States (2003).

Wang, Teng-Hao, et al., "A Novel Sweet Taste Cell-Based Sensor," *Biosensors and Bioelectronics* 26:929-934, Elsevier B.V. (2010).

\* cited by examiner

TASTE RECEPTOR INTERNALIZATION ASSAY

Each reference cited in this disclosure is incorporated herein in its entirety.

TECHNICAL FIELD

This disclosure relates generally to assays useful for identifying taste receptor modulators.

BRIEF DESCRIPTION OF THE DRAWINGS

FIG. 3A, Immunofluorescence staining of T1R2 (ThermoFisher) in NCI-H716 cells. FIG. 3B, Percentage of "Ring"-positive cells (means±SD). Recycling of T1R2 receptor correlates with decreased number of "Ring"-positive cells.

FIG. 4A, Immunofluorescence staining of GLUT4 (Sigma) in NCI-H716 cells. FIG. 4B, Percentage of "Ring"-positive cells (means±SD).

DETAILED DESCRIPTION

1. Taste Receptor Internalization Assay ("Ring Assay")

Figure 1:
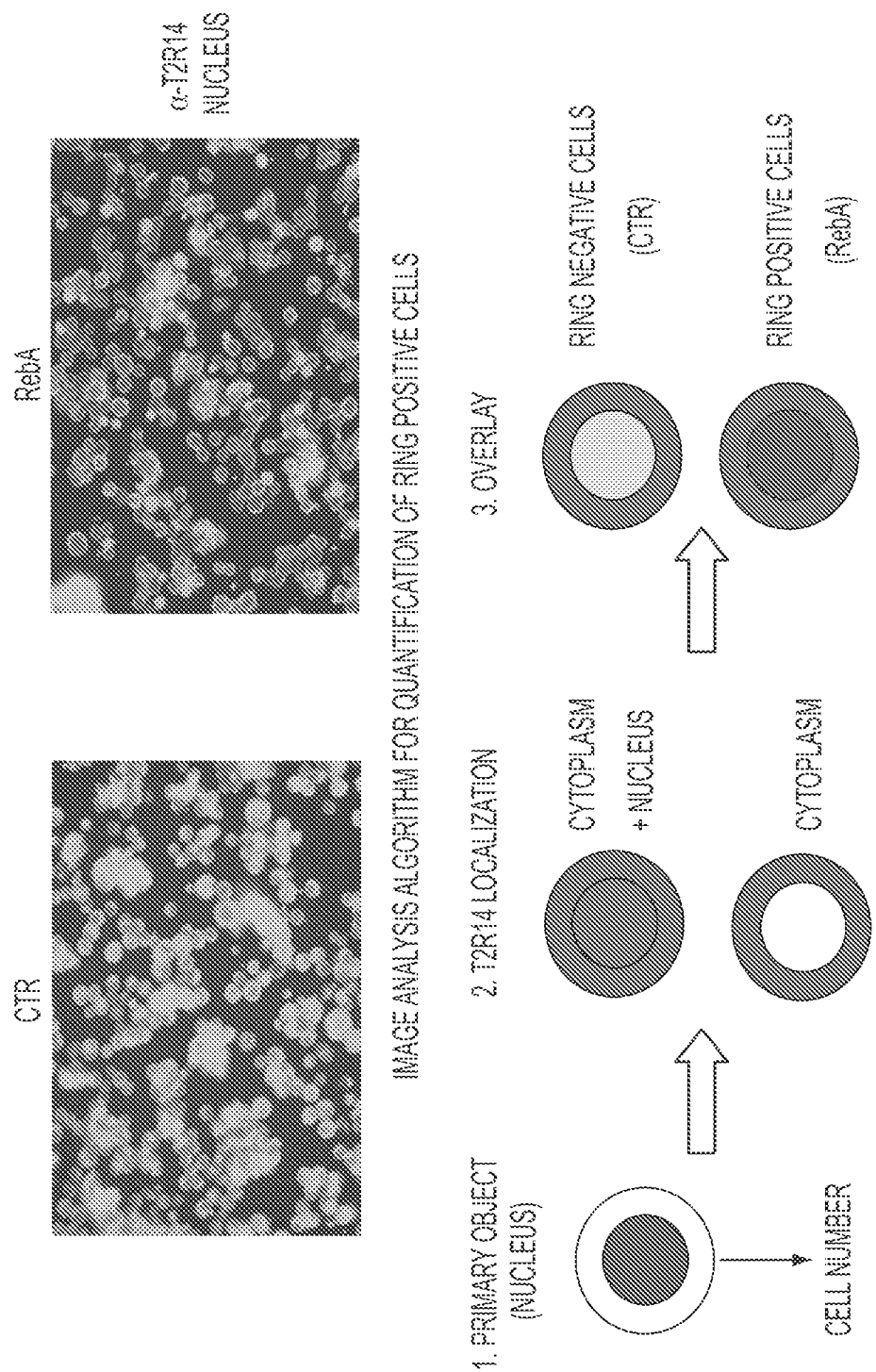
FIG. 1. Reb A treatment induces T2R14 internalization ("Ring" assay) in NCI-H716 cells. Immunofluorescence staining of T2R14 (ThermoFisher) in NCI-H716 cells.

This disclosure provides an assay for measuring taste receptor internalization. This assay, described in the specific examples, below, and shown schematically in FIG. 1, is very robust and accurately quantifies both T2R14 (a bitter receptor) and T1R2 (sweet taste receptor) localization. the assay can be used to identify sweet molecules as well as bitter blockers, and is particularly well-suited to use in high-throughput assays.

The internalization assay disclosed herein, also called a "ring assay," detects localization of receptors using antibodies specific for the receptors. A first detectable label, specific for nucleic acid (e.g., DAPI, Hoechst 33342, DRAQ5, DRAQ7, DRAQ9), is used to label cell nuclei; this labeling provides information such as the number of cells in a field and differentiates between the nuclear (e.g., DAPI-positive) and cytoplasmic (e.g., DAPI-negative) compartments. Antibodies which specifically bind to a taste receptor are used in conjunction with secondary antibodies conjugated with a second detectable label which can be differentiated from the first detectable label (e.g., FITC, TRITC, Cy3, Cy5, Alexa 350, 488, 546, 555, 568, 594, 633, 647). Diffuse circle staining is observed in the absence of a stimulus (e.g., in the presence of buffer alone). In the presence of a stimulus, however, a "ring" of internalized receptors is visualized. In some embodiments, ring-positive cells are calculated by correlation coefficient for pixel values of the nuclear and receptor signals. The extent of internalization can be expressed as percentage (mean±SD) of cells showing a continuous ring staining from multiple (e.g., quadruplicate) data points.

i. Sweet Taste Receptor

In some embodiments, the ring assay is used to detect internalization of e.g., T1R2, T1R3, or GLUT4. Co-expression of T1R2 and T1R3 results in a taste receptor that responds to sweet taste stimuli, including naturally occurring and artificial sweeteners. Sweet ligands bind to the T1R2/T1R3 receptor and activate G-protein pathway transduction, which includes receptor internalization and intracellular calcium mobilization, as well as induction of down-stream targets such as the phosphorylation of ERK1/2. Sweet taste receptors are described, for example, in U.S. Pat. No. 7,402,400. Antibodies which specifically bind to sweet taste receptors are commercially available or can be generated using methods well known in the art.

ii. Bitter Taste Receptors

In some embodiments, the ring assay is used to detect internalization of a bitter receptor, such as, e.g., T2R1, T2R3, T2R4, T2R5, T2R7, T2R8, T2R9, T2R10, T2R13, T2R14, T2R16, T2R38, T2R39, T2R40, T2R41, T2R42, T2R43, T2R44 (T2R31), T2R45, T2R46, T2R47 (T2R30), T2R48 (T2R19), T2R49 (T2R20), T2R50, and T2R60. Expression of T2R14 and other bitter receptors results in a taste receptor that responds to bitter taste stimuli, including bitter aspects of naturally occurring and artificial sweeteners. Bitter ligands bind to bitter receptors and activate G-protein pathway transduction, which includes receptor internalization and intracellular calcium mobilization, as well as induction of down-stream targets. Bitter taste receptors are described, for example, in U.S. Pat. No. 7,022,488. Antibodies which specifically bind to bitter receptors are commercially available or can be generated using methods well known in the art.

iii. Test Compounds

Test compounds can be naturally occurring or synthetically produced. Proteins, polypeptides, peptides, polysaccharides, and small molecules are examples of test compounds that can be screened using methods disclosed herein.

iv. Cells

Any cell that comprises or can be engineered to comprise a functional taste receptor can be used in a ring assay. In some embodiments, NCI-H716 cells are used (ATCC catalog # CCL-251). These cells express the bitter receptors T2R1, T2R3, T2R4, T2R5, T2R7, T2R8, T2R9, T2R10, T2R13, T2R14, T2R16, T2R38, T2R39, T2R40, T2R41, T2R42, T2R43, T2R44 (T2R31), T2R45, T2R46, T2R47 (T2R30), T2R48 (T2R19), T2R49 (T2R20), T2R50, and T2R60, the sweet receptor T1R2/T1R3, α-gustducin, and the glucose transporter GLUT4. Other cells can be engineered to express T2R14, T1R2/T1R3 α-gustducin, and/or GLUT4 using methods well known in the art. GLUT4 is described, inter alia, in U.S. Pat. No. 7,799,538 and references cited therein. See U.S. Pat. No. 8,338,115 and references cited therein and Adler et al., Cell 100, 693-702, 2000 for descriptions of α-gustducin.

Other cells that can be used in the disclosed assay include, but are not limited to, 1A2, ARH-77, RWPE-1, WI-38, EJM, NCI-H1155, L-1236, NCI-H526, JM1, SHP-77, SNU-878, NCI-H2196, C3A, CA46, SNU-466, KS-1, SNU-738, MOLP-2, HDLM-2, Pfeiffer, HCC-15, Alexander cells, L-540, KMS-12-BM, JK-1, NCI-H1092, SW 1990, NCI-H1184, SU-DHL-1, Hep 3B2.1-7, P3HR-1, NCI-H2029, SU-DHL-5, SNU-1, MOLP-8, SUP-M2, MONO-MAC-1, SNU-1040, KYM-1, HEC-59, HCC1569, OCI-LY3, Hs 819.T, DU4475, CI-1, S-117, OVCAR-8, SNU-626, HL-60, SUIT-2, T3M-4, RKO, MOR/CPR, DK-MG, GA-10, OCUM-1, HCT-15, HT, MONO-MAC-6, G-402, Toledo, COV362, SU-DHL-8, Daoy, NCI-H1435, LS513, Hs 839.T, Hs 172.T, BT-483, KMS-21BM, AGS, NCI-H2172, LC-1/sq-SF, SNU-201, NUGC-4, SK-HEP-1, SUP-B15, SNU-5, HT-1197, SUP-T1, AMO-1, KU812, AN3 CA, AML-193, VMRC-RCW, HLE, HuH28, Hs 751.T, NCI-H2110, MEG-01, MV-4-11, Hep G2, KYSE-30, KALS-1, BICR 6, RMUG-S, JHH-6, Ki-JK, IST-MES1, HCC-95, HPB-ALL, HSC-3, 697, LOU-NH91, KARPAS-299, GI-1, COLO 792, SK-N-FI, D341 Med, HGC-27, SR-786, COLO-818, MHH-CALL-2, SF126, NCI-H322, A-253, NCI-H1623, MCF7, HCC-44, FU97, OCI-LY-19, Hs 766T, NCI-H522, RL, HCC1428, RPMI 6666, U-937, NCI-H460, SW 1088, NCI-H1792, NCI-H1693, UACC-257, JHUEM-2, HuT 78, UACC-893, NCI-H929, A-704, OV56, LN-229, OE19, SK-MEL-24, RD-ES, NCI-H211, KCI-MOH1, NCI-H1963, Hs 706.T, ChaGo-K-1, EPLC-272H, OPM-2, KHM-1B, A549, HuGl-N, NCI-H508, MHH-CALL-3, SNU-1076, A3/KAW, MEL-HO, TO 175.T, Caki-1, Hs 936.T, SK-LU-1, WM-983B, K-562, EFE-184, SNU-520, NCI-H2291, HCC-1195, ABC-1, KE-39, NH-6, HCC2218, CMK, RS4;11, KYSE-450, OV7, KYSE-510, SK-UT-1, SNU-C1, OE33, P12-ICHIKAWA, DLD-1, COV434, HuNS1, SNU-899, SW480, COLO-678, LU99, KOPN-8, NCI-H2227, SW1463, Hs 675.T, JHH-4, NCI-H1703, HEC-1-A, BDCM, MIA PaCa-2, PC-3, TE-15, PK-45H, MKN-45, HCC-366, CAL-29, HEC-50B, CPC-N, KMRC-20, SW1116, EOL-1, COLO 205, EHEB, YD-38, MC116, SK-N-BE(2), BV-173, NCI-H2347, LU65, RT4, U-87 MG, LK-2, KP-N-YN, HEC-251, NCI-H1651, GP2d, RERF-LC-MS, NB-4, NCI-H2286, SNU-61, T-47D, huH-1, KYSE-180, ST486, SW 1353, M-07e, KASUMI-1, YH-13, NCI-H28, GAMG, JeKo-1, GOS-3, SNU-324, PA-TU-8902, MFE-280, SNU-245, NALM-1, RERF-LC-Sq1, BICR 22, ZR-75-1, COR-L23, SW579, COR-L88, KM12, Hs 611.T, OUMS-23, RERF-LC-Ad1, NCI-H1385, SK-LMS-1, COLO-320, BL-70, GRANTA-519, MCAS, Panc 08.13, AM-38, KMS-11, SIG-M5, SNU-407, JHOS-2, OVCAR-4, Set-2, OV-90, MeWo, HEL, HT-29, MDA-MB-231, TOV-21G, NCI-H1355, KMS-27, NALM-6, KMS-26, Caov-4, KASUMI-2, UACC-62, U266B1, Hs 695T, HT55, BICR 31, TCC-PAN2, KMS-20, Hs 578T, RI-1, Hs 606.T, NCI-H1341, THP-1, BCP-1, Hs 737.T, SW1417, MOLT-4, Raji, ESS-1, MEL-JUSO, SH-10-TC, Hs 683, ME-1, EB2, PLC/PRF/5, NCI-H1339, A4/Fuk, SEM, HEC-265, IST-MES2, KE-97, NCI-H1437, COLO-704, NCI-H1915, TE-5, NCI-H2023, NCI-H82, T1-73, SNU-840, HuT 102, NCI-H1944, KYSE-520, Kasumi-6, 1321N1, Hs 742.T, IM95, PL45, CL-40, WM1799, KMM-1, SNU-449, JHUEM-1, KARPAS-620, Loucy, SNU-1079, Daudi, HCC-56, HSC-2, COR-L47, PA-TU-8988S, OAW28, COR-L311, L-363, Malme-3M, NOMO-1, Hs 870.T, SU-DHL-10, Hs 229.T, NCI-H810, KYSE-410, RPMI-8402, SNU-175, EBC-1, RVH-421, K029AX, PA-TU-8988T, LXF-289, OVSAHO, CAL-12T, Hs 940.T, MM1-S, SUP-HD1, LNCaP clone FGC, HSC-4, NU-DHL-1, NCI-H2228, BEN, CAL-78, Sq-1, NCI-H1793, SNU-C2A, MDA-MB-134-VI, COV318, KE-37, TYK-nu, MOTN-1, T98G, SW837, EB1, Becker, PE/CA-PJ34 (clone C12), Hs 616.T, NCI-H446, WM-88, CHP-126, Calu-1, SNU-283, NCI-H1573, SW 1271, SNU-16, JHOS-4, ACHN, Calu-3, KMRC-1, SW 1783, TE-11, TE-9, HuH-6, P31/FUJ, HT-1376, NCI-H520, 786-0, KNS-60, Caki-2, OVK18, PL-21, NCI-H2452, JURL-MK1, TEN, JHH-7, MDA-MB-157, Calu-6, RKN, NUGC-2, ONS-76, J82, OUMS-27, SNU-1196, Hs 739.T, RPMI-7951, NCI-H854, JHH-5, JVM-2, Hey-A8, 5637, KYSE-140, Capan-2, KYSE-150, HEC-1-B, BICR 16, HEL 92.1.7, MHH-NB-11, SNU-387, SK-OV-3, SK-MEL-28, IGROV1, ML-1, HLF-a, CHL-1, YKG1, A-204, OCI-M1, 8505C, JVM-3, NCI-H647, DB, COLO-800, PK-59, FaDu, HLF, OVMANA, EFO-27, PF-382, NCI-H747, LS123, SU-DHL-6, SJRH30, PANC-1, NCI-H2342, KM-H2, DND-41, HH, HuCCT1, F-36P, DMS 454, Hs 274.T, AU565, NCI-H1666, EN, RH-41, NCI-H1373, NCI-H838, SK-MEL-30, MOLM-6, DEL, NCI-H226, NCI-H1648, NCI-H661, 143B, Mino, C32, KMS-34, NCI-H1694, SK-ES-1, UACC-812, GDM-1, NCI-H23, Panc 02.03, CCF-STTG1, LOX IMVI, SJSA-1, MDST8, PK-1, NCI-H716, SU-DHL-4, MPP 89, MJ, COLO 829, PE/CA-PJ15, HD-MY-Z, BxPC-3, WM-793, COLO 668, T84, JHOM-1, PEER, LS411N, GMS-10, KMBC-2, RMG-I, KELLY, SNU-761, NALM-19, HEC-151, G-361, OVTOKO, A-498, SW 900, LCLC-103H, FTC-133, QGP-1, Reh, CMK-11-5, NU-DUL-1, BT-20, Hs 600.T, Hs 604.T, KATO III, SNU-410, NCI-H2126, SK-MEL-5, MDA-MB-468, AsPC-1, HUP-T3, KP-N-SI9s, L-428, SNU-1105, HUP-T4, 769-P, LMSU, NCI-H1869, NCO2, MOLM-16, CAL 27, HCC70, NCI-H1930, COV644, Hs 863.T, HCC-2279, D283 Med, Hs 944.T, HCC1599, MDA-MB-415, HCC2157, NCI-H1618, SNU-308, HCC1954, DMS 153, HPAF-II, T24, CJM, VM-CUB1, UM-UC-3, LAMA-84, NCI-H1734, JHH-2, VMRC-RCZ, MFE-319, MDA-MB-453, SNU-503, TOV-112D, B-CPAP, GSU, HCC-78, NCI-H2171, CAMA-1, HEC-108, HCC4006, CAL-85-1, NCI-H2122, COLO-699, NCI-H196, LUDLU-1, SW 780, RPMI 8226, LP-1, PC-14, HuTu 80, T.T, SW948, 22Rv1, HARA, NCI-H596, IPC-298, SCaBER, NCI-H1838, NB-1, Hs 934.T, Hs 895.T, DMS 114, KYSE-70, KP-3, KP4, DAN-G, NCI-H2009, OC 316, SCC-25, U-138 MG, RCC10RGB, MFE-296, NCI-H1755, RERF-LC-KJ, 8305C, WSU-DLCL2, ES-2, MSTO-211H, SCC-15, ZR-75-30, PSN1, SNU-423, NCI-H2106, TE-1, UT-7, KMS-28BM, NCI-H2081, SK-MM-2, COLO 741, OC 314, HCC1395, MOLT-13, LN-18, Panc 10.05, PE/CA-PJ41 (clone D2), Hs 746T, CW-2, SKM-1, NUGC-3, TE-10, NCI-H358, NCI-H69, BFTC-909, HOS, BICR 18, NCI-H1395, OVKATE, Hs 698.T, EFM-19, COLO-783, MHH-CALL-4, ACC-MESO-1, NCI-H1436, KP-N-RT-BM-1, SK-MEL-31, NCI-H1105, CAL-51, YD-15, NCI-H2085, NCI-H2444, HCC1187, Hs 939.T, CAL-120, SCC-9, TUHR14TKB, KMRC-2, KG-1-C, ECC10, CGTH-W-1, NCI-H841, C2BBe1, SUP-T11, RCH-ACV, CADO-ES1, JURKAT, 647-V, SK-MEL-2, MDA-MB-175-VII, MKN74, SNU-C4, LCLC-97TM1, SCC-4, BHY, IGR-37, KYO-1, Hs 281.T, TT, TUHR4TKB, HT-1080, NCI-H660, TE 441.T, LS1034, KNS-42, Panc 04.03, HCC1419, AZ-521, SNG-M, NCI-N87, G-292, clone A141B1, KPL-1, MDA-MB-361, CL-14, NCI-H2170, HuH-7, RD, NCI-H2066, IGR-1, TE-14, VCaP, BL-41, SNU-620, SK-MES-1, MEC-2, NCI-H1299, IGR-39, RT112/84, SF-295, DV-90, A2780, BICR 56, NCI-H510, NCI-H2141, YD-8, NCI-H2405, TF-1, MEC-1, CCK-81, NCI-H1048, Hs 822.T, NCI-H2052, K052, CAL-54, Hs 840.T, SW620, SK-CO-1, BT-474, CL-11, KNS-62, NCI-H1650, G-401, MOLT-16, SNU-398, COLO-680N, EM-2, Hs 294T, CAL-62, KMRC-3, A101D, KG-1, BT-549, HT115, A-375, SW-1710, WM-115, KLE, JHUEM-3, MKN7, CHP-212, HCC202, BC-3C, NCI-H1568, KMS-18, PE/CA-PJ49, COLO-849, SIMA, OCI-AML3, GSS, EC-GI-10, EFO-21, RCM-1, DMS 273, KU-19-19, RERF-GC-1B, SH-4, SK-MEL-3, RERF-LC-Ad2, M059K, JHOM-2B, MDA PCa 2b, Hs 852.T, RL95-2, Panc 03.27, SNU-216, Panc 02.13, CFPAC-1, SK-N-SH, OCI-AML2, LoVo, SBC-5, NCI-H1876, NCI-H441, SK-N-AS, COR-L24, HCC38, NCI-H1781, DOHH-2, NCI-H1563, U-251 MG, HPAC, JIMT-1, U-2 OS, A-673, TC-71, NCI-H650, NIH:OVCAR-3, CAS-1, JL-1, SK-MEL-1, MDA-MB-4355, Ishikawa (Heraklio) 02 ER-, TE 617.T, SU.86.86, RERF-LC-AI, TT2609-C02, LS 180, YAPC, HDQ-P1, KNS-81, FU-OV-1, KP-2, DMS 53, SNU-1272, Detroit 562, 42-MG-BA, L3.3, COLO-679, NCI-H2087, NCI-H2030, GCT, NCI-H889, Caov-3, MDA-MB-436, NCI-H524, MKN1, KCL-22, Capan-1, CML-T1, H4, NCI-H727, Hs 343.T, MHH-ES-1, NMC-G1, HCC-1171, REC-1, Hs 618.T, A172, YD-10B, SW48, MUTZ-5, TE-6, JHH-1, HCT 116, TE-4, IA-LM, MG-63, NCI-H1975, TALL-1, HCC1806, HMCB, SCLC-21H, HCC1500, CL-34, Panc 05.04, SW403, TM-31, HCC1937, JMSU-1, DMS 79, SNB-19, NCI-H1836, Li-7, HCC827, 639-V, MOLM-13, SK-BR-3, IMR-32, TUHR10TKB, OAW42, SK-N-MC, TGBC11TKB, NCI-H1581, EFM-192A, YMB-1, HCC2935, ECC12, HCC-33, DU 145, NCI-H146, SNU-1214, SNU-1077, 23132/87, HT-144, SNU-182, Hs 888.T, SNU-475, GCIY, Hs 729, JHOC-5, SW 1573, HEC-6, OCI-AML5, Hs 688(A).T, Hs 821.T, PCM6, RT-112, SK-N-DZ, SNU-478, SNU-119, HCC1143, NCI-H209, 8-MG-BA, COR-L105, COR-L95, SNU-46, COV504, CAL-148, SNU-05, DBTRG-05MG, BHT-101, WM-266-4, BFTC-905, KYSE-270, TE-8, SNU-213, U2-OS, and SH-SY5Y.

2. Ring Assays Using NCI-H716 Cells

In some embodiments, NCI-H716 cells are used to detect cellular responses to potential bitter blockers. NCI-H716 cells are contacted with a test compound. Internalization of a bitter receptor in the presence of the test compound indicates the test compound is a potential bitter taste modulator. Bitter taste modulators can be included in various consumables, including foods, beverages, and pharmaceuticals.

In some embodiments, NCI-H716 cells are used to detect cellular responses to sweet tastants (e.g., molecules which themselves evoke a sweet taste or which enhance a sweet taste). NCI-H716 cells are contacted with a test compound. Internalization of T1R2 indicates the test compound is a sweet molecule. Sweet molecules can be included in various consumables, including foods, beverages, and pharmaceuticals.

Example 1

High-Content Imaging Assay for T2R14 Internalization
Cell Culture, Materials.

NCI-H716 cell were grown in RPMI1690 media supplemented with 10% fetal bovine serum. Cells were seeded at density of 20,000 cells/well on PDL-coated 384-well plates. Rabbit anti-T2R14 antibodies and rabbit anti-T1R2 antibodies were from ThermoFisher. Alexa 488-conjugated antibodies and Hoechst 33342 were from Life Technology.
Compound Treatment.

20,000 cells in PBS+10% FBS were plated on clear-bottom, PDL-coated, black-wall 384-well plates suitable for HCA imaging. For T2R14 studies compounds were added to the cells. Stock solutions of all compounds were diluted in dimethyl sulfoxide (DMSO) and used at 10 mM. Control groups of cells also received DMSO (0.1%) in medium.
Ring Assays.

NCI-H716 cells were stimulated with RebA (Purecircle) at 10 mM for indicating time points at 37° C. The cells were then fixed and processed for indirect immunofluorescence with antibodies against bitter receptor T2R14. All images were acquired with a 20× objective using ImageXpress Micro automated microscope. Hoechst 33342 staining is pseudo-colored blue and antibody specific staining is pseudo-colored green. Overlaid images indicate diffuse circle staining upon treatment with buffer; treatment of NCI-H716 cells with Reb A resulted in "Ring"-staining "Ring"-positive cells were calculated by correlation coefficient for pixel values of the Hoechst 33342 (nuclear) and FITC (T2R14) signals. The extent of internalization is expressed as the percentage (means±S.D.) of cells showing a continuous "Ring" staining from quadruplicate data points. Recycling of T2R14 receptor correlates with decreased number of "Ring"-positive cells.

Statistical analyses and graphs were made with Tibco Spotfire or GraphPad Prism.

Figure 2:
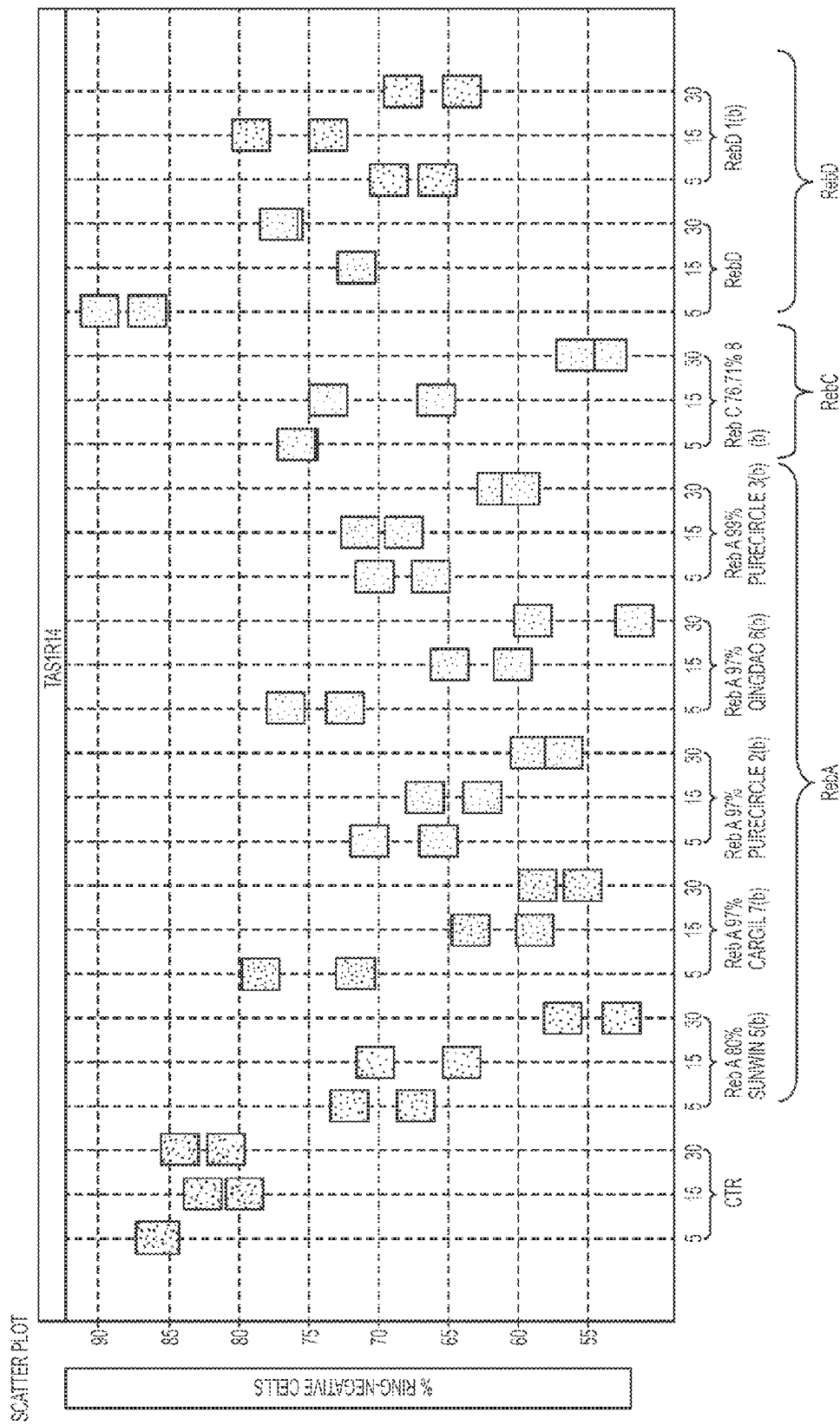
FIG. 2. Percentage of "Ring"-positive cells upon treatment with RebA (means±SD).

In the ring assay assay, when T2R14 receptors are stained with specific antibodies, we observed the majority of T2R14 receptors at the cell surface, which resulted in a diffuse circle staining. When the cells were treated with RebA or RebC, receptor internalization and trafficking of T2R14 occurred, resulting in "Ring"-staining Using Multiwaves Translocation scoring analysis algorithm (Molecular Devices), we demonstrated that T2R14 internalization increases after stimulation of NCI-H716 cells with RebA or RebC. In contrast, the internalization was not observed upon treatment with RebD. This example demonstrates a link between high-content imaging cell-based assays and sensory data, thereby providing an in vitro mechanism-based approach that can be used to discover novel bitter blockers. The results are shown in FIG. 2.

Example 2

High-Content Imaging Assay for T1R2 Internalization

Figure 3A:
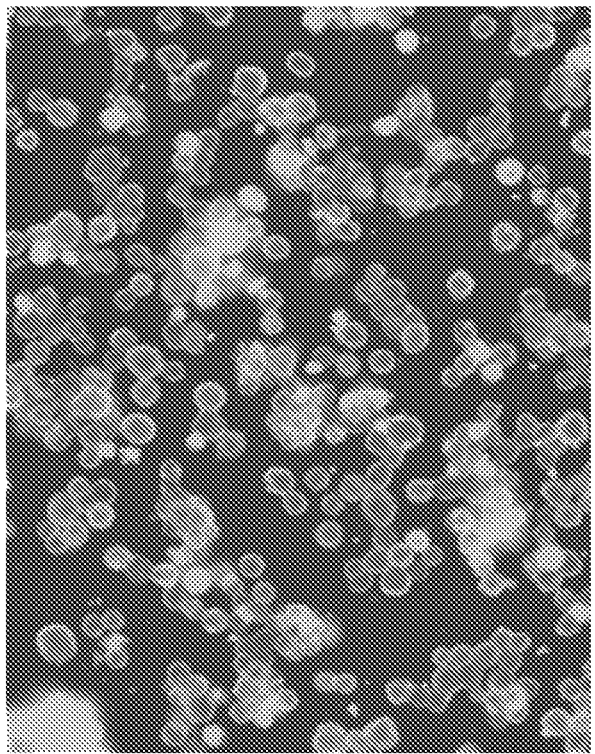
FIGS. 3A-B. Ring-formation assay, T1R2 internalization.
Figure 3A:
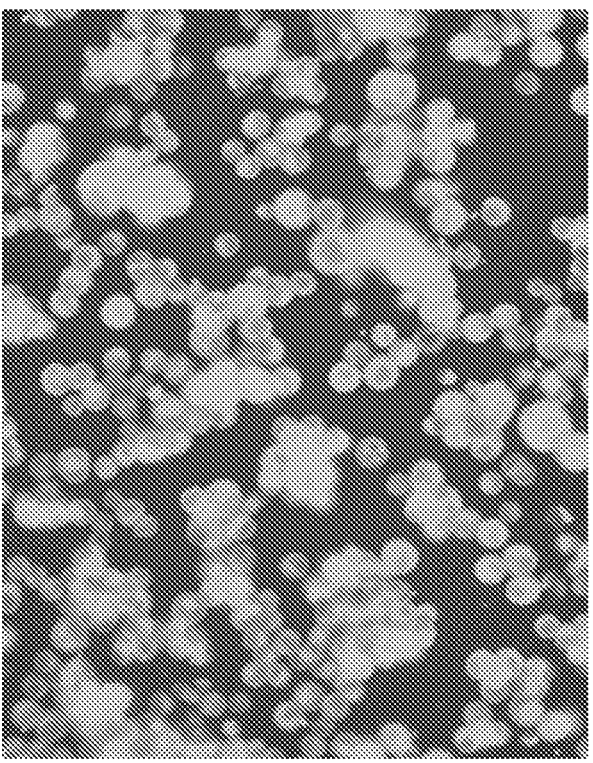
Figure 3B:
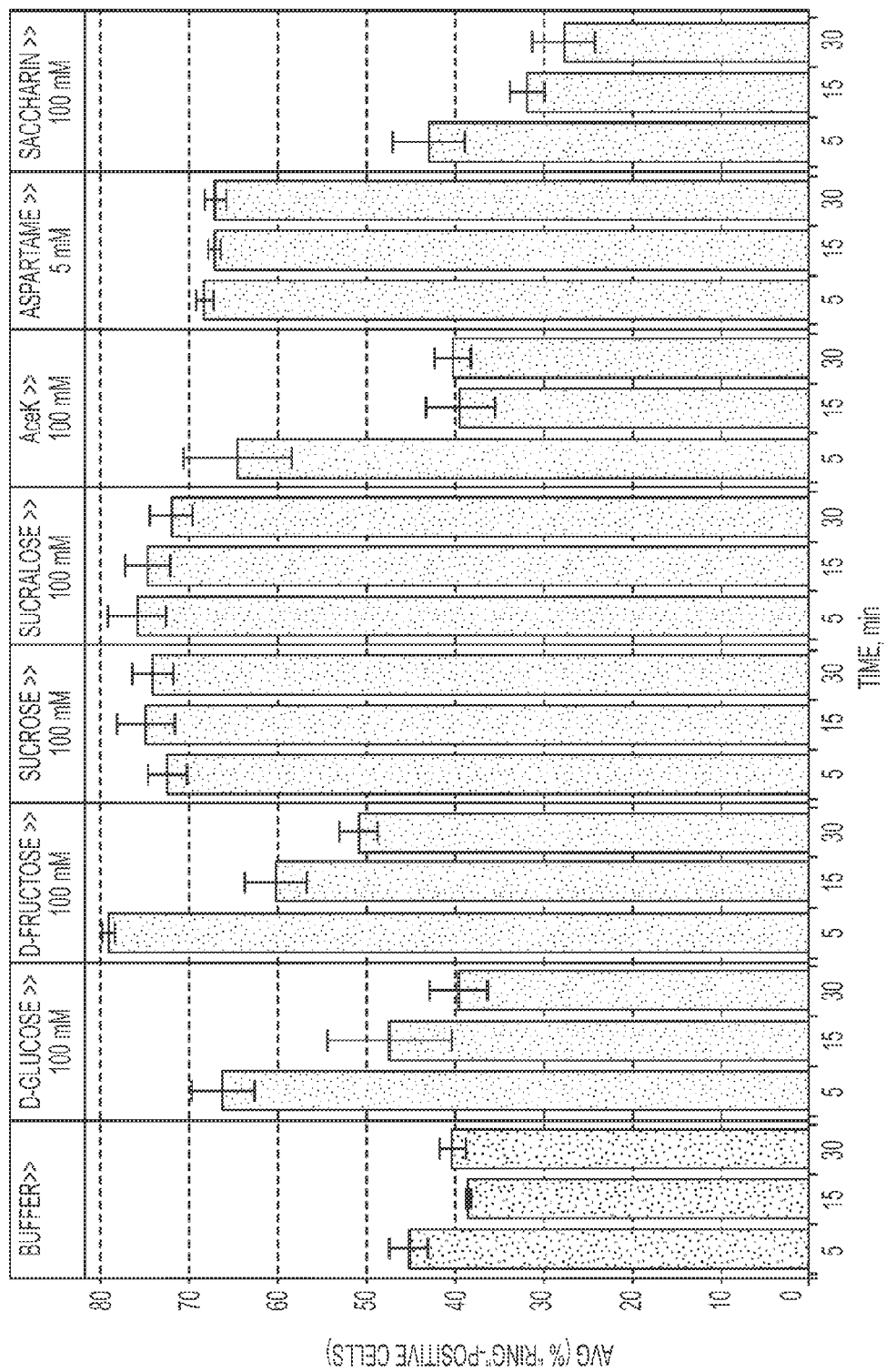

We investigated the effects of sweet compounds on the human enteroendocrine cell line NCI-H716 that endogenously expresses sweet receptor T1R2/T1R3 and α-gustducin. Untreated NCI-H716 cells expressed T1R2 receptors at the cell-surface. Treatment with D-glucose induced T1R2 receptor internalization, resulting in typical "Ring"-staining (FIG. 3A). Using Multiwaves Translocation Module, we quantitated internalization of endogenous T1R2 in NCI-H716 cells treated with sweet-tasting compounds. T1R2 internalization increased after stimulation with D-glucose, D-fructose, sucrose, sucralose, aspartame, and Ace-K, whereas T1R2 internalization process was not observed upon treatment with saccharine (FIG. 3B).

A correlation was observed between the molecular structures of sugars and T1R2-recycling routes. Thus, T1R2 recycled back to the cell membrane very quickly upon treatment with monosaccharaides, D-glucose and D-fructose, whereas slow T1R2-recycling was observed with the disaccharide sucrose and its analog sucralose (FIG. 3B).

Example 3

High-Content Imaging Assay for GLUT4 Internalization

Recently, sensory and animal studies provided evidence that additional receptors to sweet taste may exist, especially responsive to artificial compounds, such as saccharine. We hypothesized that glucose transporter GLUT4 (Entrez Gene # 6517) might be an upstream molecule in saccharine signaling in NCI-H716 cells. GLUT4 is expressed preferentially in T1R3-positive taste cells and GLUT4 internalization is a key mechanism for the regulation of glucose uptake in the absence of insulin. NCI-H716 cells express endogenous GLUT4 (Oncomine database), which may mediate the observed $Ca^{(2+)}$ response in these cell lines.

Figure 4A:
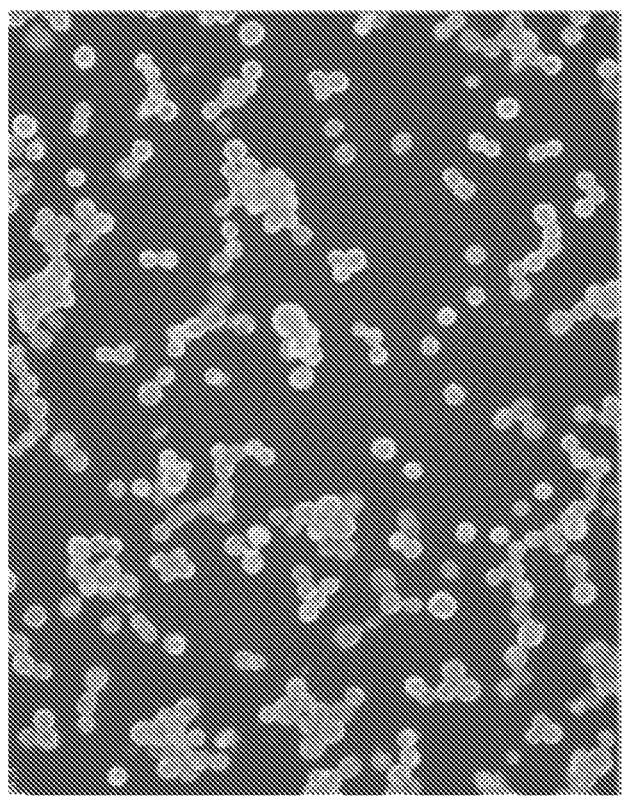
FIGS. 4A-B. GLUT4 is a common receptor for artificial sweeteners.
Figure 4A:
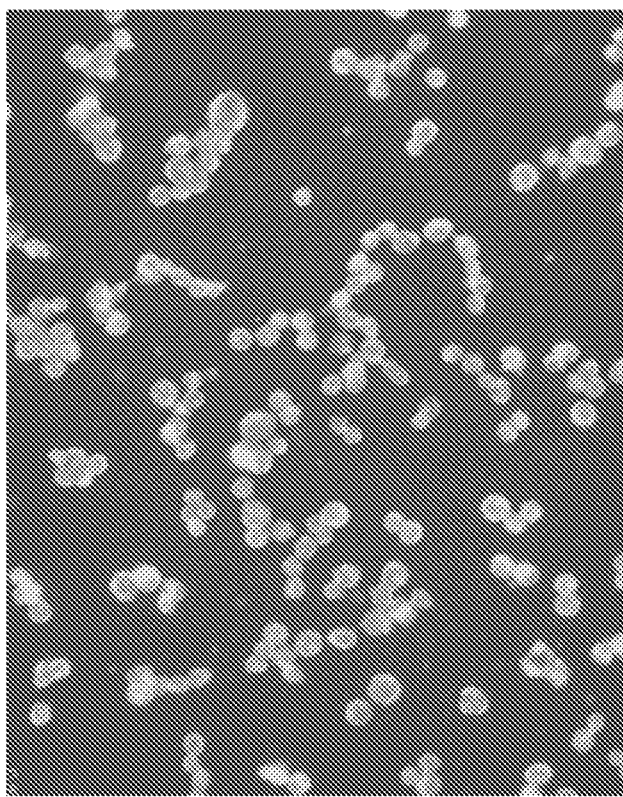
Figure 4B:
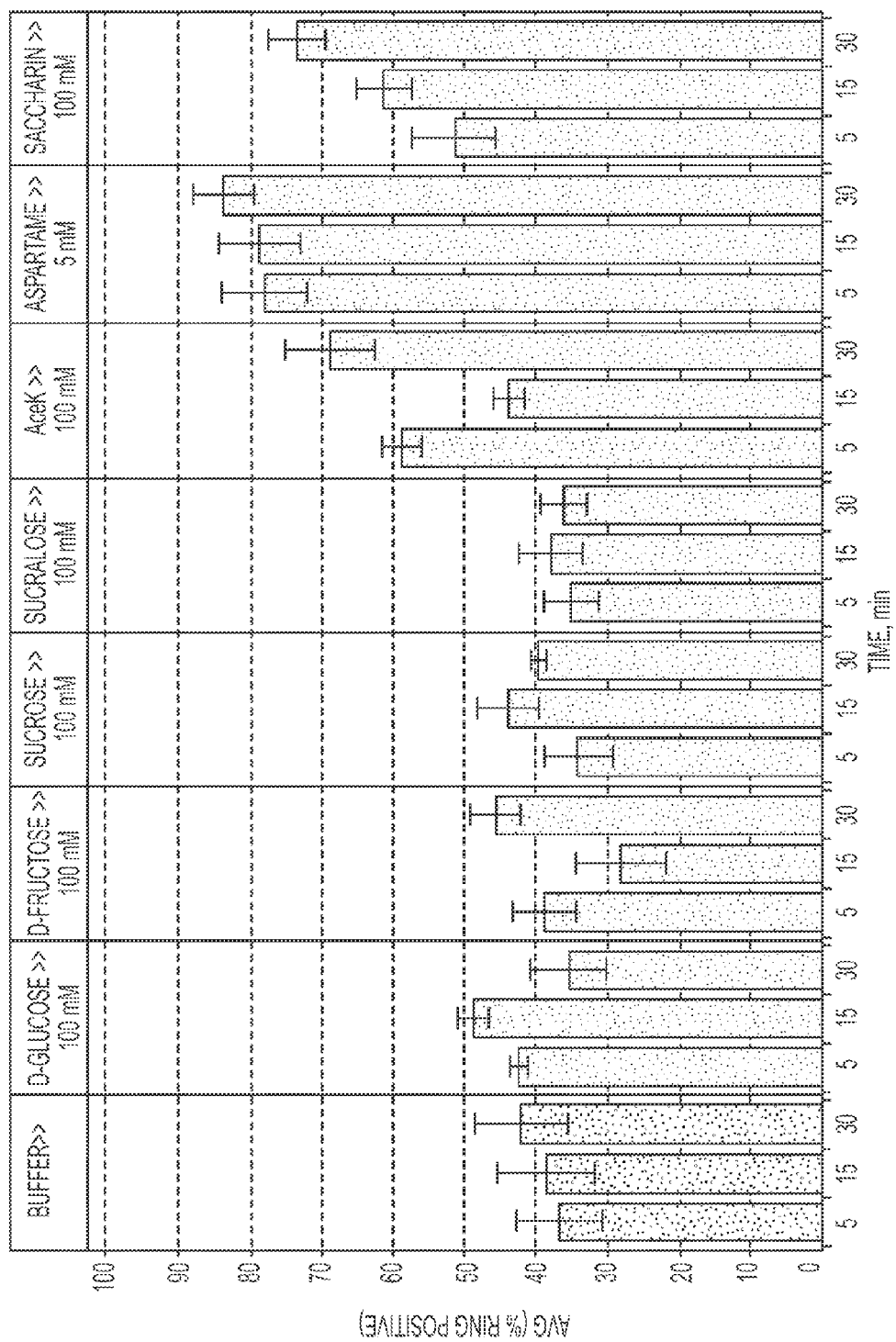

To explore further the role of GLUT4 in signaling by artificial sweeteners, we tested internalization of endogenous GLUT4 in NCI-H716 cells. Treatment with saccharine led to a rapid redistribution of GLUT4 within the cell, resulting in "Ring"-staining (FIG. 4A). Quantitation of GLUT4 internalization, measured as an increased number of "Ring"-positive cells, has demonstrated that GLUT4 internalization increased after stimulation with Ace-K, aspartame, and saccharine, whereas natural sugars were not able to activate GLUT4 internalization process (FIG. 4B).

Taken together, these results suggest that GLUT4 is the common receptor for artificial sweeteners. Saccharin activates $Ca^{(2+)}$ response via GLUT4 only, whereas Ace-K and aspartame target both T1R2/T1R3 and GLUT4 pathways.

The invention claimed is:

1. A method of identifying a taste modulator comprising:
   a) contacting a cell comprising a functional taste receptor with a test compound;
   b) contacting the cell with a first reagent comprising a detectable label specific for a cell nucleus and with a second reagent comprising a second detectable label specific for the taste receptor; and
   c) detecting internalization of the taste receptor, wherein internalization of the taste receptor in the presence of the test compound indicates the test compound is a potential taste modulator.

2. The method of claim 1, wherein the taste receptor is a sweet taste receptor.

3. The method of claim 2, wherein the sweet taste receptor comprises T1R2.

4. The method of claim 2, wherein the sweet taste receptor comprises T1R3.

5. The method of claim 2, wherein the sweet taste receptor is GLUT4.

6. The method of claim 1, wherein the taste receptor is a bitter taste receptor.

7. The method of claim 6, wherein the bitter taste receptor is selected from the group consisting of T2R1, T2R3, T2R4, T2R5, T2R7, T2R8, T2R9, T2R10, T2R13, T2R14, T2R16, T2R38, T2R39, T2R40, T2R41, T2R42, T2R43, T2R44 (T2R31), T2R45, T2R46, T2R47 (T2R30), T2R48 (T2R19), T2R49 (T2R20), T2R50, T2R60, and combinations thereof.

8. The method of any of claims 1-7, wherein the cell is an NCI-H716 cell.

* * * * *